United States Patent
Sekiyama et al.

[11] Patent Number: 5,965,447
[45] Date of Patent: Oct. 12, 1999

[54] PRETREATING APPARATUS FOR ANALYTIC CONTAINER AND AUTOMATIC FILLING SYSTEM

[75] Inventors: Shigetoshi Sekiyama, Yokohama; Toshikazu Ogawa, Tokyo; Shigeyuki Koike, Tokyo; Toyoki Sugiyama, Tokyo; Yasunobu Horiguchi, Tokyo, all of Japan

[73] Assignee: Shigetoshi Sekiyama, Kanagawa, Japan

[21] Appl. No.: 09/131,823

[22] Filed: Aug. 10, 1998

Related U.S. Application Data

[62] Division of application No. 08/809,777, filed as application No. PCT/JP95/01978, Sep. 28, 1995, abandoned.

[30] Foreign Application Priority Data

Sep. 28, 1994 [JP] Japan ................................. 6-233750

[51] Int. Cl.[6] .................................................. G01N 35/10
[52] U.S. Cl. ........................... 436/49; 436/50; 436/174; 436/180; 422/63; 422/67; 422/100; 422/105; 422/106; 141/94; 141/95; 141/128; 141/198
[58] Field of Search ........................... 422/62, 63, 67, 422/81, 100, 105, 106, 108, 110; 436/43, 49, 50, 55, 180, 179, 174; 141/94, 95, 128, 198

[56] References Cited

U.S. PATENT DOCUMENTS

| | | | |
|---|---|---|---|
| 3,120,125 | 2/1964 | Vasel | 73/290 |
| 3,192,968 | 7/1965 | Baruch et al. | 141/82 |
| 3,622,279 | 11/1971 | Moran | 422/65 |
| 3,713,338 | 1/1973 | Kind | 73/293 |
| 3,849,830 | 11/1974 | Wagner | 15/302 |
| 4,227,886 | 10/1980 | Bullock et al. | 23/230 R |
| 4,314,970 | 2/1982 | Stein et al. | 422/72 |
| 4,444,598 | 4/1984 | Sakagami | 134/22.12 |
| 4,635,665 | 1/1987 | Namba et al. | 134/167 R |
| 5,073,720 | 12/1991 | Brown | 250/577 |
| 5,331,850 | 7/1994 | Loos | 73/293 |
| 5,452,076 | 9/1995 | Schopper et al. | 356/128 |

FOREIGN PATENT DOCUMENTS

| | | |
|---|---|---|
| 54-36878 | 11/1979 | Japan. |
| 58-82625 | 6/1983 | Japan. |
| 61-34424 | 2/1986 | Japan. |
| 3-85453 | 10/1991 | Japan. |
| 5-80060 | 3/1993 | Japan. |

*Primary Examiner*—Long V. Le
*Attorney, Agent, or Firm*—Schwegman, Lundberg Woessner & Kluth, P.A.

[57] ABSTRACT

A filling process for filling an analytic liquid in a container is optically accurately and automatically carried out using a laser beam. An automatic filling system is capable of automatically and continuously cleaning and drying the container in pretreating processes prior to an analysis.

7 Claims, 12 Drawing Sheets

DIVERGENT LIGHT

PARALLEL LASER BEAM

RELATIONSHIP BETWEEN ANALOG OUTPUT AND SHIELDED AREA

PRETREATING APPARATUS FOR ANALYTIC CONTAINER AND AUTOMATIC FILLING SYSTEM

This application is a divisional application of U.S. patent application Ser. No. 08/809,777, filed Jun. 12, 1997 (the '777 Application), now abandoned which is 937 of PCT/JP95/01978 filed Sep. 28, 1995. The '777 Application is incorporated herein by reference.

TECHNICAL FIELD

The present invention relates to an automatic filling system for automatically filling a solution in a container and automatically and continuously pretreating an analytic container used in a filling process.

BACKGROUND ART

Typically in chemical research and development activities, it is being practiced to dissolve various materials into inorganic or organic solvents to make solutions and effect analyses using such solutions, and hence it is necessary to prepare various many solutions. Under the circumstances, there has been a demand for automatizing analytic systems in order to win the competition among researchers and developers by simply and quickly carrying out analytic processes.

In such analytic processes, materials to be analyzed and solvents are poured into a number of containers such as measuring flasks to prepare target amounts of solutions and hold them in the containers. A target amount of solution cannot be obtained simply by dissolving a certain amount of material into a certain amount of solvent. Therefore, it is necessary to perform a filling process for holding a target amount of solution in a container.

Since the filling process is difficult to automatize, however, it is difficult to fully automatize an analytic system in its entirety.

The filling process is a process for filling a solution up to a line called a marked line on a container under certain conditions. An error of the filling process depends on how the level of the solution in the container deviates from the marked line. The filling process is an important task which eventually determines the value of a series of analytic operations. Consequently, the filling process needs to be carried out strictly, and hence is a process which the person in charge has to be most careful about among various analytic operations and which cannot be neglected.

The above strict requirements for the filling process have been one of various factors which have made it difficult to automatize the filling process. The filling process that need delicate adjustments has imposed burdens with respect to time and labor on those involved in the filling process.

Another factor is that the conventional detecting technology is not available for automatically detecting a marked line on containers and automatically detecting solution levels in containers with high accuracy. According to the conventional detecting technology, a level sensor or a float switch is used to detect a solution level from above or detect a solution level in direct contact with the solution. Though these detecting processes have been studied so far, they have proven unsatisfactory as they are not preferable from the standpoint of the filling process.

In view of the conventional drawbacks, it has been proposed to optically detect a marked line and a solution level (including its meniscus) with a laser beam, for example, and carry out a filling process using a detected signal.

Apparatus which use a laser beam to detect a marked line and a meniscus are expected to suffer various detection interferences depending on how to process actual samples. Specifically, the solution sample in a container when it is filled in the container tends to a) become turbid, b) produce bubbles, and c) become attached to the container wall in pretreating operations. Since these defects are an obstacle to the transmission of detected light of the laser beam, i.e., irregularly reflect or block such detected light, they are liable to interfere with the detection of the marked line and the meniscus. As a result, the accuracy with which the marked line and the meniscus are detected is low, and hence the accuracy of the filling process is not highly reliable.

Proposals for eliminating these interferences have been to A) keep the solution clear by centrifugal separation and filtering, B) remove bubbles from the solution with a debubblizer such as alcohol or the like, and C) clean the inner surface of the container with a solvent.

These processes A)~C) have to be carried out with respect to many containers when various many solutions are to be prepared. The processes B) and C) have heretofore been carried out manually, and hence pretreating operations for analyses have been inefficient and imposed strong burdens with respect to time and labor. At present, it is difficult to automatize and effect these pretreating processes continuously.

DISCLOSURE OF THE INVENTION

The present invention has been made in an effort to solve the above conventional problems. It is an object of the present invention to provide an automatic filling system including a pretreating apparatus for automatically and continuously carrying out at least one of a debubblizing process, a cleaning process, and a drying process as pretreating processes on an analytic container to be filled with an analytic liquid, for thereby preventing obstacles from being developed to the transmission of detected light through the container and for allowing the container to be filled with the liquid automatically with high optical accuracy.

According to the present invention, an automatic filling system for automatically carrying out a filling process to fill a solution, which comprises a material to be analyzed that is dissolved in a solvent, up to a desired position based on a marked line on a container, comprises:

a container having a marked line and including a transparent portion where the marked line is present;

liquid pouring means for pouring a given liquid into the container;

laser beam emitting means for emitting a parallel laser beam to the portion of the container;

laser beam detecting means for detecting the laser beam emitted from the laser beam emitting means and having passed through the container, to detect an amount of the laser beam having passed through the container; and pouring control means for controlling the liquid pouring means based on the amount of the laser beam which has been detected by the laser beam detecting means, to fill the liquid up to the desired liquid level based on the marked line.

For carrying out the filling process more efficiently, the automatic filling system further includes auxiliary liquid level detecting means for detecting an auxiliary liquid level at least below the marked line on the container, and preliminary pouring means for filling the liquid up to the auxiliary liquid level in the container through detection by the auxiliary liquid level detecting means prior to the filling process.

A pretreating apparatus for an analytic container, which is included in the automatic filling system, comprises:

container holding and moving means for holding a container to hold a sample liquid as an object to be analyzed and moving the container;

a first nozzle body for ejecting a cleaning liquid;

cleaning liquid ejecting means for ejecting the cleaning liquid from the first nozzle body;

a second nozzle body for ejecting a gas;

gas ejecting means for ejecting the gas from the second nozzle body;

nozzle body moving means for moving the first and second nozzle bodies and setting the first and second nozzle bodies in respective positions;

container position control means for controlling the container holding and moving means to move and position the container successively closely to the first and second nozzle bodies set in the respective positions; and ejection control means for controlling the cleaning liquid ejecting means to eject the cleaning liquid from the first nozzle body into the container which has been positioned closely to the first nozzle body by the container holding and moving means, for thereby cleaning the container, and thereafter controlling the gas ejecting means to eject the gas from the second nozzle body into the container which has been positioned from the first nozzle closely to the second nozzle body by the container holding and moving means, for thereby removing the cleaning liquid from the container.

If the container is supplied with a solvent together with the object to be analyzed according to a filling process, for thereby producing and holding a target amount of solution, then the pretreating apparatus further includes a third nozzle body for ejecting a debubblizing solution to remove bubbles which are formed in the solution in the container in the filling process, and debubblizing solution ejecting means for ejecting the debubblizing solution from the third nozzle body.

BEST MODE FOR CARRYING OUT THE INVENTION

Embodiments of the present invention will be described in detail below with reference to the drawings.

Figure 1:
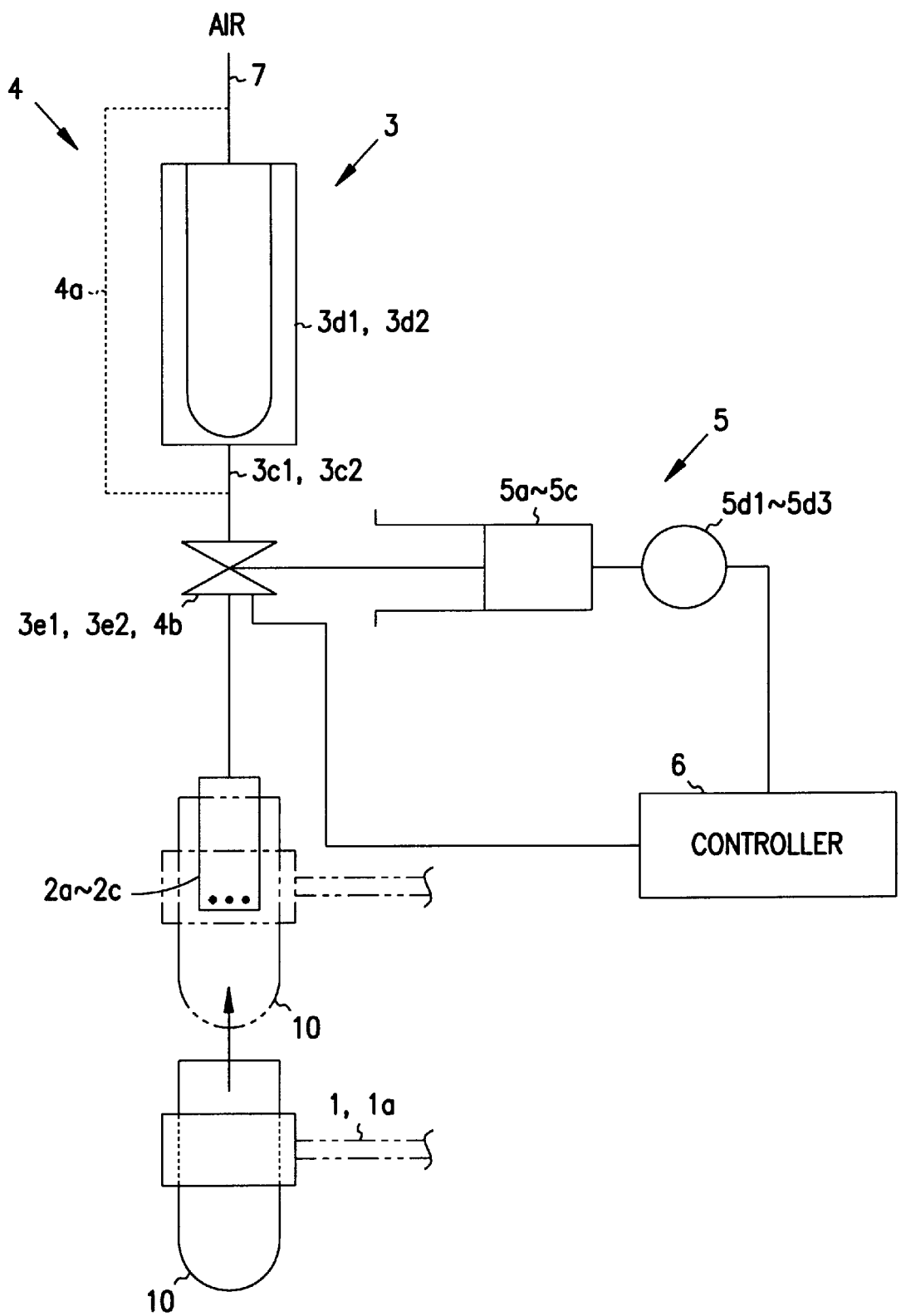
FIG. 1 is a schematic diagram showing a general arrangement of an analytic container pretreating apparatus according to a preferred embodiment of the present invention.
Figure 2A:
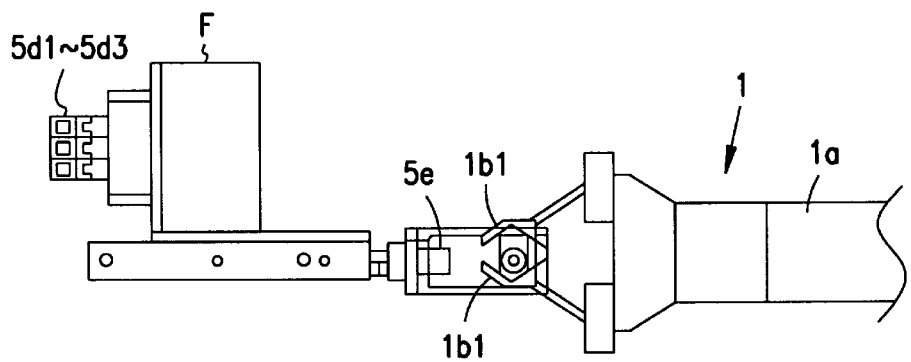
FIG. 2(a) is a plan view of a mechanical structure of the analytic container pretreating apparatus.
Figure 2B:
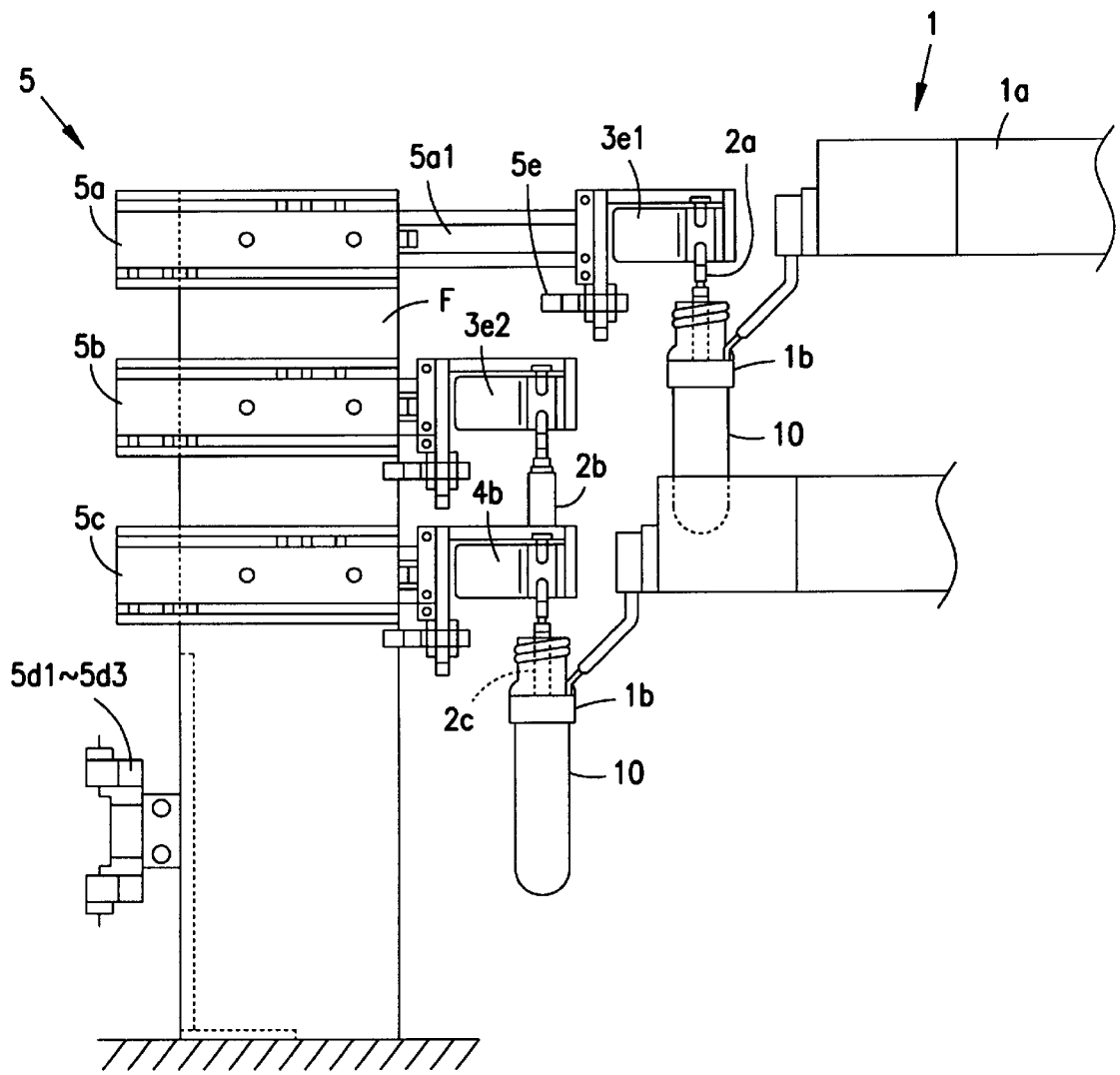
FIG. 2(b) is a side elevational view of the mechanical structure of the analytic container pretreating apparatus.
Figure 3:
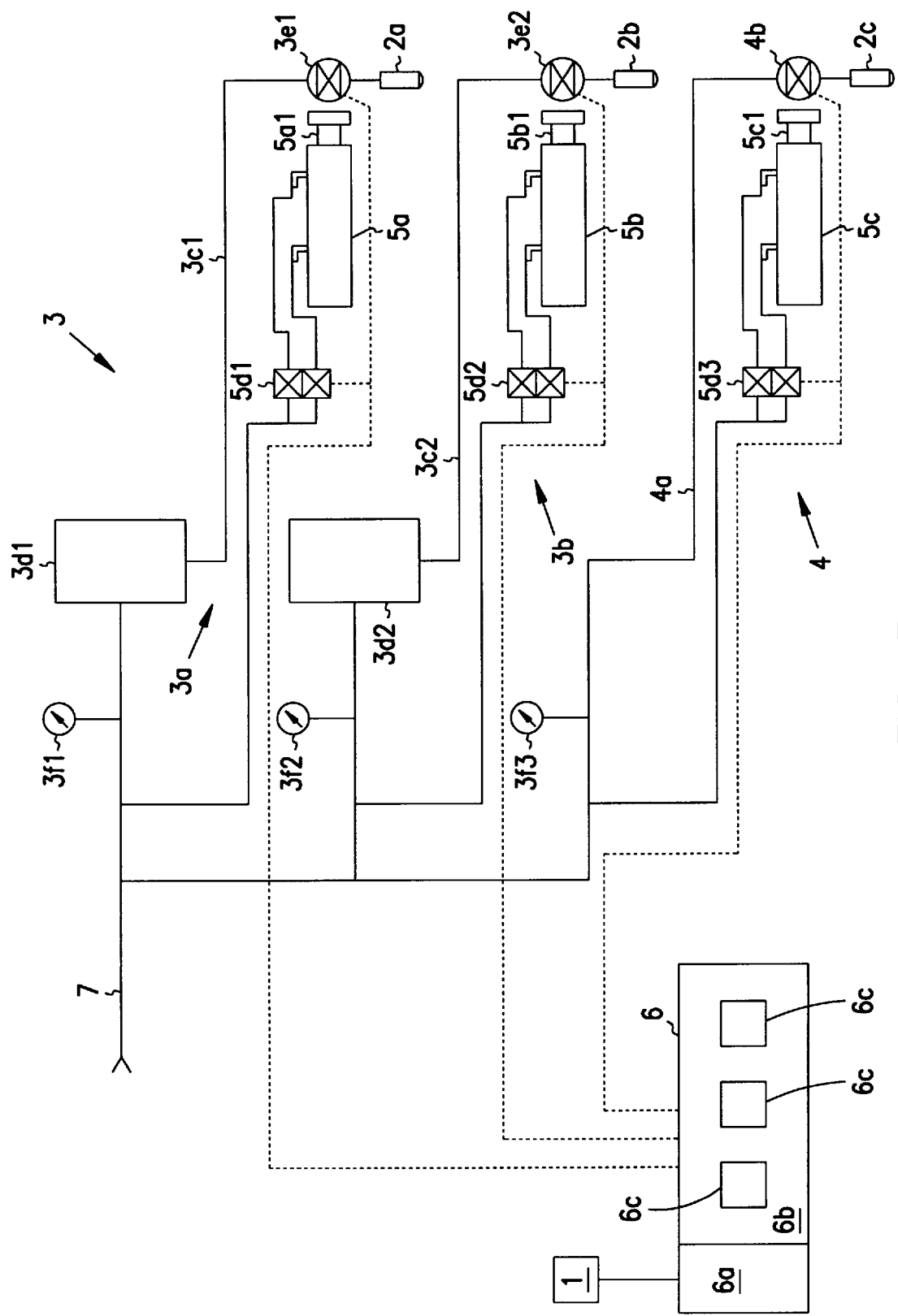
FIG. 3 is a schematic diagram showing various pipes and a control system of the analytic container pretreating apparatus.
Figure 4C:
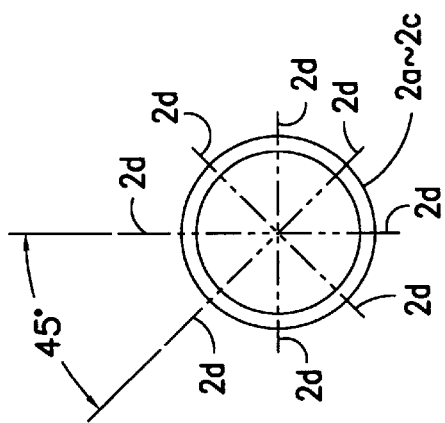
FIG. 4(c) is a bottom view of the nozzle body.
Figure 4A:
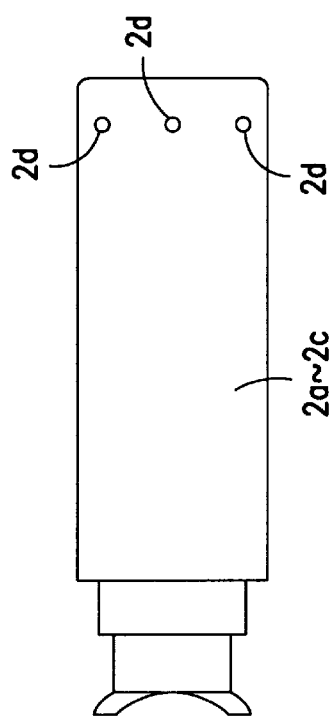
FIG. 4(a) is a side elevational view of a nozzle body which can be employed in the analytic container pretreating apparatus.
Figure 4B:
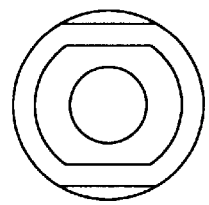
FIG. 4(b) is a plan view of the nozzle body.
Figure 5A:
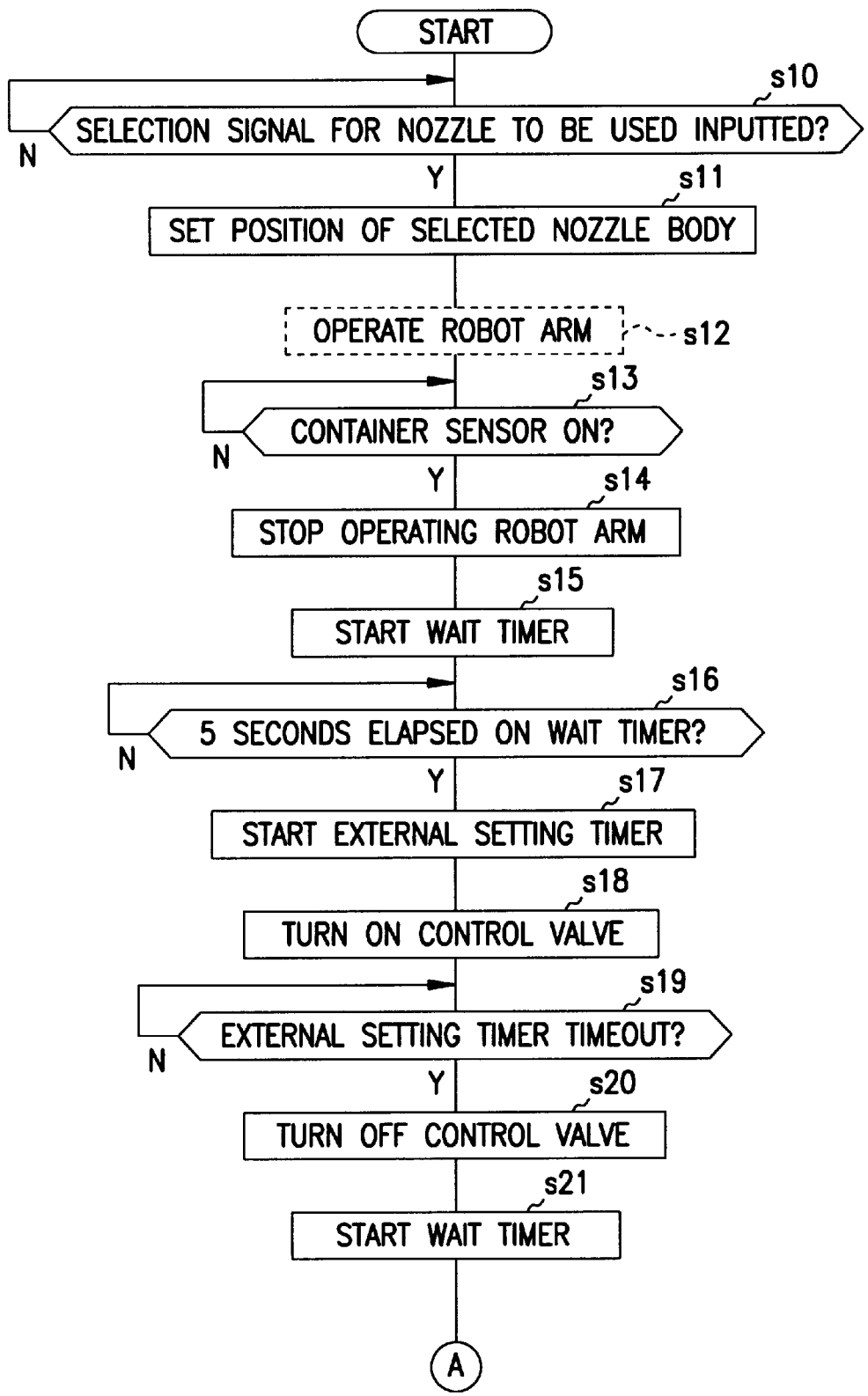
FIG. 5 is a flowchart of a control sequence of the analytic container pretreating apparatus.
Figure 5B:
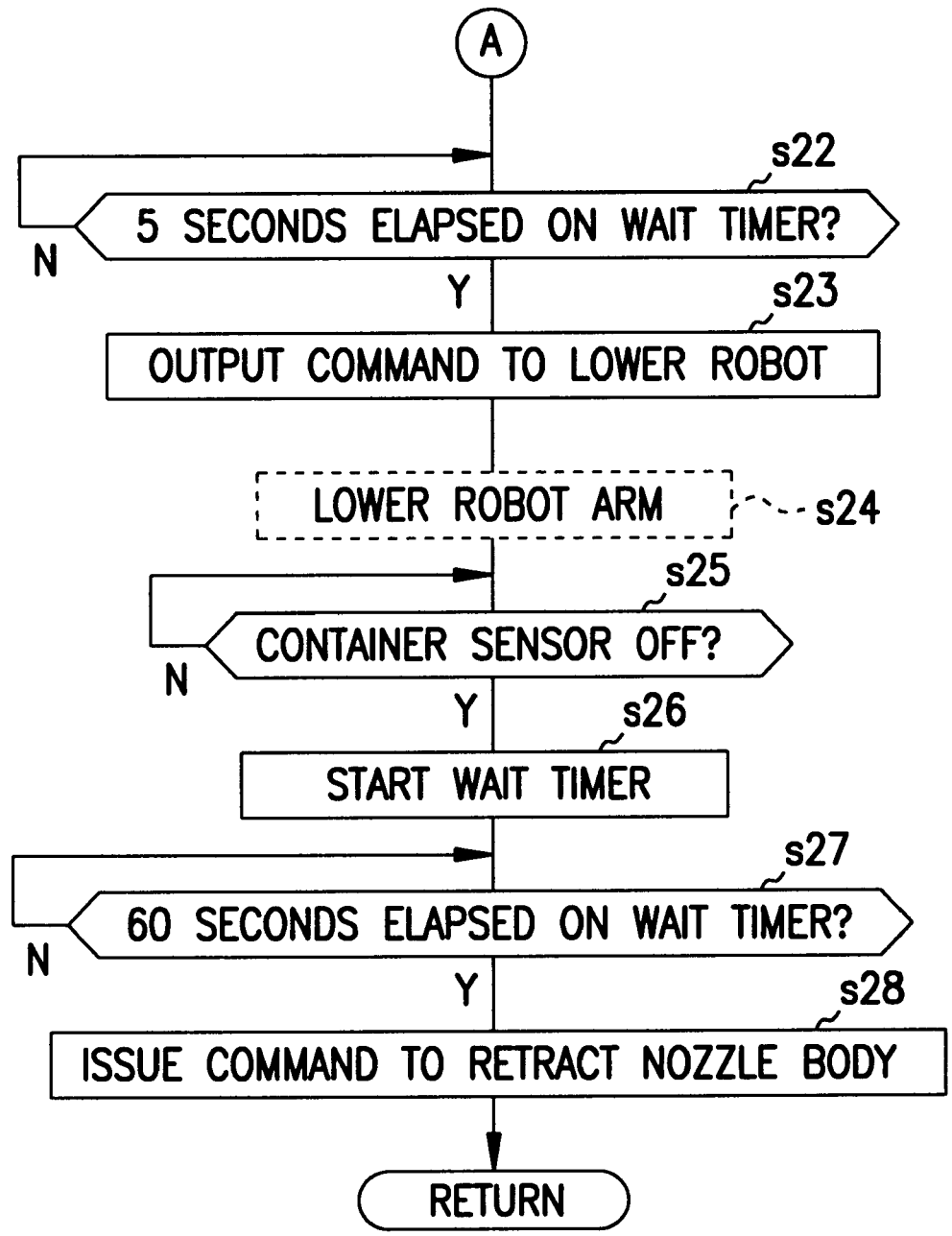

FIGS. 1 through 5 show an analytic container pretreating apparatus according to a preferred embodiment of the present invention for pretreating an analytic container with a marked line in an automatic filling system. FIG. 1 is a schematic diagram showing an overall arrangement of the analytic container pretreating apparatus; FIGS. 2(a) and 2(b) are plan and side elevational views of a processing section of the analytic container pretreating apparatus; FIG. 3 is a schematic diagram showing various pipes and a control system of the analytic container pretreating apparatus, FIGS. 4(a)~4(c) are illustrative of a nozzle body; and FIG. 5 is a flowchart of a control sequence of the analytic container pretreating apparatus.

The analytic container pretreating apparatus mainly comprises a feed robot (corresponding to holding and moving means) 1, nozzle bodies (corresponding to first and second nozzle bodies) 2a~2c, liquid ejectors 3a, 3b, a gas ejector 4, nozzle body moving units 5a~5c, and a unit controller 6. The analytic container pretreating apparatus automatically carries out a series of operations including debubblizing, cleaning, and drying processes on an analytic container 10 with a marked line.

The analytic container pretreating apparatus also has a compressed air supply source 7 which is supplied with compressed air from an air compressor (not shown). In FIGS. 2(a) and 2(b), the analytic container pretreating apparatus has a main frame F.

The marked container 10 serves to hold an analytic liquid as a sample, and is transmissive of a laser beam in the vicinity of a marked line 10a. Details of the analytic container 10 will be described later on.

The feed robot 1 holds the marked container 10 with chucks 1b of a grip hand on the tip end of an arm 1a, and moves the marked container 10. The feed robot 1 may comprise any of various known robots. The chucks 1b serve to grip and hold the marked container 10 against droppage. As shown in FIG. 2(a), the chucks 1b comprise two chuck plates 1b1, of an angular shape in plan, disposed in confronting relation to each other and movable to change the distance therebetween. The distance between the chuck plates 1b1 is reduced or increased to grip or release the marked container 10.

The holding and moving means according to the present invention is not limited to the type described above. For example, the structure of the means for holding the container may be selected or modified in various ways. The means for holding the container may be of a bucket structure, for example, for surrounding the container from below.

The nozzle bodies 2 include a cleaning nozzle body 2a for ejecting a cleaning liquid, a debubblizing nozzle body 2b for ejecting debubblizing alcohol, and a drying nozzle body 2c for ejecting drying air. Since the nozzle bodies 2a~2c are arranged in juxtaposed relation, they can automatically perform a series of operations, i.e., a cleaning process, a debubblizing process, and a drying process, and complete them in a short period of time.

As shown in FIGS. 4(a), 4(b), 4(c), each of the nozzle bodies 2a~2c has a substantially cylindrical shape having an outside diameter (e.g., 9 mm) which can be inserted into the marked container 10. The nozzle body has 8 nozzle orifices 2d for ejecting a liquid or a gas which are defined in a tip end thereof (the end inserted into the marked container 10) in a circumferential pattern at equal angular intervals of 45°. Since the nozzle orifices 2d are arranged in the circumferential direction, the nozzle bodies 2a~2c can eject a cleaning liquid, alcohol, and compressed air radially toward an inner circumferential surface of the marked container 10 to clean, debubblize, and dry it highly efficiently. The nozzle bodies 2a~2c which has the small outside diameter (9 mm) is suitable for cleaning the marked container 10 which has a small inside diameter.

The array and number of nozzle orifices may be selected otherwise. For example, one array of nozzle orifices should preferably contain 1~16 nozzle orifices, and more preferably contain 8 equal spaced nozzle orifices. If nozzle orifices are arranged in a plurality of arrays spaced along the axis of the nozzle body, then the nozzle body can clean or otherwise process a wide area of the marked container 10. If the nozzle orifices 2d are arranged at irregular angular intervals, then the nozzle body can eject a cleaning liquid in a concentrated manner to a local area to be cleaned. A variety of diameters may be available for the nozzle orifices 2d under conditions for cleaning, etc. In the embodiment, the nozzle orifices 2d have a diameter of 0.2 mm, for example.

The liquid ejectors 3a, 3b eject a cleaning liquid and alcohol from the nozzle bodies 2a, 2b, respectively, and the gas ejector 4 ejects air from the corresponding nozzle body 2c.

The liquid ejectors 3a, 3b comprise respective reservoir tanks 3d1, 3d2 for storing a cleaning liquid and alcohol, respectively, and supplying them to the respective nozzle bodies 2a, 2b under the pressure of compressed air supplied from the compressed air supply source 7, and respective control valves 3e1, 3e2 such as ON/OFF solenoidcontrol valves for selectively opening and closing pipes 3c1, 3c2 extending from the reservoir tanks 3d1, 3d2 to the nozzle bodies 2a, 2b.

The gas ejector 4 comprises a control valve 4b such as an ON/OFF solenoid-control valve for selectively opening and closing a pipe 4a extending from the compressed air supply source 7 to the nozzle body 2c.

In the embodiment, the pressure of the compressed air supplied from the compressed air supply source 7 can be adjusted by adjustment gages 3f1, 3f2, 3f3. Therefore, the intensity with which the cleaning liquid, alcohol, and air are ejected can be varied. Therefore, it is possible to establish an ejecting pressure optimum for cleaning, debubblizing, and drying the inner wall surface of the marked container 10 to provide large cleaning, debubblizing, and drying effects. The reservoir tanks 3d1, 3d2 are in the form of cartridges that can easily be replaced with other cartridges having changed contents. Consequently, they are suitable for use in applications where various solvents are used as a cleaning liquid, alcohol, etc. A wide variety of solvents can be used with the reservoir tanks 3d1, 3d2.

The reservoir tanks 3d1, 3d2 can store solvents which are objects to be analyzed, and can withstand air pressures.

The nozzle body moving units 5 serve to move the nozzle bodies 2a~2c in a horizontal direction, and are associated respectively with the nozzle bodies 2a~2c. In the embodiment, as shown in FIGS. 2(a), 2(b) and 3, the nozzle body moving units 5 comprise respective cylinders 5a~5c having respective cylinder rods 5a1~5c1 with the nozzle bodies 2a~2c fixed thereto, the cylinder rods 5a1~5c1 being movable back and forth to position the nozzle bodies 2a~2c, and cylinder actuating valves 5d1~5d3 such as solenoid-operated valves for supplying compressed air to and discharging compressed air from the cylinders 5a~5c.

The cylinders 5a~5c have respective horizontal axes and arranged in a vertical array at equally spaced intervals so that they are superposed one on the other when viewed in plan. Container sensors 5e are mounted on the respective tip ends of the cylinder rods 5a1~5c1 in fixed positional relation to the nozzle bodies 2a~2c, for detecting when marked containers 10 that have moved closely to the nozzle bodies 2a~2c are positioned in covering relation to the nozzle bodies 2a~2c.

The means for positioning the nozzle bodies 2a~2c is not limited to the above moving means, but may be means for fixedly positioning the nozzle bodies 2a~2c. In such a modification, the containers are moved with respect to the fixed nozzle bodies by the holding and moving means.

The unit controller 6 are operated by predetermined means to automatically carry out a series of pretreating operations including cleaning, debubblizing, and drying processes, i.e., to control the feed robot 1 (robot control stage 6a) to move marked containers 10 into positions near the cleaning nozzle body 2a, the debubblizing nozzle body 2b, and the drying nozzle body 2c, respectively, output a control signal to the liquid ejectors 3 to eject a cleaning liquid and alcohol from the cleaning nozzle body 2a and the debubblizing nozzle body 2b into the marked containers 10 in the close positions for thereby cleaning the marked containers 10, and also output a control signal to the gas ejector 4 to eject compressed air from the drying nozzle body 2c for drying away the cleaning liquid (pretreatment control stage 6b).

The pretreatment control means 6b of the unit controller 6 has ejection timers 6c which can externally be set to ejection times for the respective nozzle bodies 2a~2c.

The unit controller 6 may comprise any of various control means such as a sequence controller, a programmable controller, a personal computer, or the like, which can store a predetermined control sequence and control the feed robot 1, the liquid ejectors 3, the gas ejector 4, and the nozzle body moving units 5 according to the control sequence.

Operation of the pretreating apparatus according to the embodiment will be described below with reference to FIGS. 1~4 and FIG. 5. FIG. 5 shows a flowchart of a control sequence of the analytic container pretreating apparatus. In FIG. 5, steps are represented by s10~s28, and the operation of the pretreating apparatus is shown by solid lines whereas the operation of the feed robot 1 by broken lines.

The unit controller 6 stores the control sequence shown in FIG. 5 as a software program in its memory, or as a hardware sequence for a sequence circuit.

Since the nozzle bodies 2a, 2b, 2c carry out a series of operations including cleaning, debubblizing, and drying processes, they are controlled by the control sequence of the flowchart.

First, a selection signal for selecting either one of the nozzle bodies 2a, 2b, 2c is inputted to the unit controller 6 (s10). At this time, the selection signal is inputted from the control stage 6a of the feed robot 1.

Then, the unit controller 6 applies an operation signal to a corresponding one of the cylinder actuating valves 5d1~5d3 based on the inputted selection signal, moving forward the selected nozzle body 2a~2c to an established position (s11). If the established position is at the rear stroke end of the cylinder 5a~5c, then the cylinder 5a~5c remain in its original position.

While the marked container 10 is being gripped by the chucks 1b, the unit controller 6 actuates the arm 1a to lift the marked container 10 (s12). When the upper end of the marked container 10 is detected by the container sensor 5e (s13), the unit controller 6 stops actuating the arm 1a (s14).

Then, the unit controller 6 starts a built-in wait timer in the pretreatment control stage 6b (s15). After a wait time of 0.5 second (s16), the unit controller 6 starts the ejection timer 6c (s17), and turns on the control valves 3e1, 3e2, 4b (s18). While the control valves 3e1, 3e2, 4b are being turned on, any of a cleaning liquid, alcohol, and air is ejected from the nozzle bodies 2a, 2b, 2c to carry out any of one of the cleaning, debubblizing, and drying processes.

Upon elapse of the time to which the ejection timer 6c has been set (s19), the unit controller 6 turns off the control valves 3e1, 3e2, 4b (s20).

After a wait time of 0.5 second measured by the wait timer (s21, s22), the unit controller 6 outputs a command signal to lower the arm 1a to the feed robot 1 (s23). The arm 1a of the feed robot 1 is operated (s24) to lower the chucked marked container 10. After the container sensor 5e is turned off (s25), the unit controller 6 operates the wait timer (s26). After a wait time of 60 seconds (s27), the unit controller 6 outputs a retraction command signal to the operating one of the cylinder actuating valves 5d1 ~5d3, thereby retracting the advanced one of the cylinder rods 5a1~5c1 (s28). The advanced one of the nozzle bodies 2a~2c is retracted back to its original position.

One of the pretreating process for the marked container 10 is finished. When another one of the nozzle bodies 2a~2c is selected, the unit controller 6 will repeat the above operation (s10~s28) for the selected one of the nozzle bodies 2a~2c.

After all the nozzle bodies 2a~2c are selected, no selection signal is inputted to the unit controller 6, and the series of operations comes to an end.

In the above embodiment, a solvent required to dissolve an object material to be analyzed is ejected as a cleaning liquid, and air is ejected through the control valves 3e1, 3e2, 4b controlled by the unit controller 6, and sprayed under the pressure of compressed air from the nozzle orifices 2d of the nozzle bodies 2a~2c for a given period of time.

If the above pretreating apparatus is combined with a container filling system, then it is possible to continuously and highly accurately manage volumes of samples such as tooth paste for analysis and fill such samples in containers.

Since the pretreating apparatus can be incorporated as one operating part in an LA robot system, it can be used in a wide range of applications.

A system (automatic filling system) for automatically filling the marked container 10 which has been pretreated by the pretreating apparatus described above will be described below.

Figure 6:
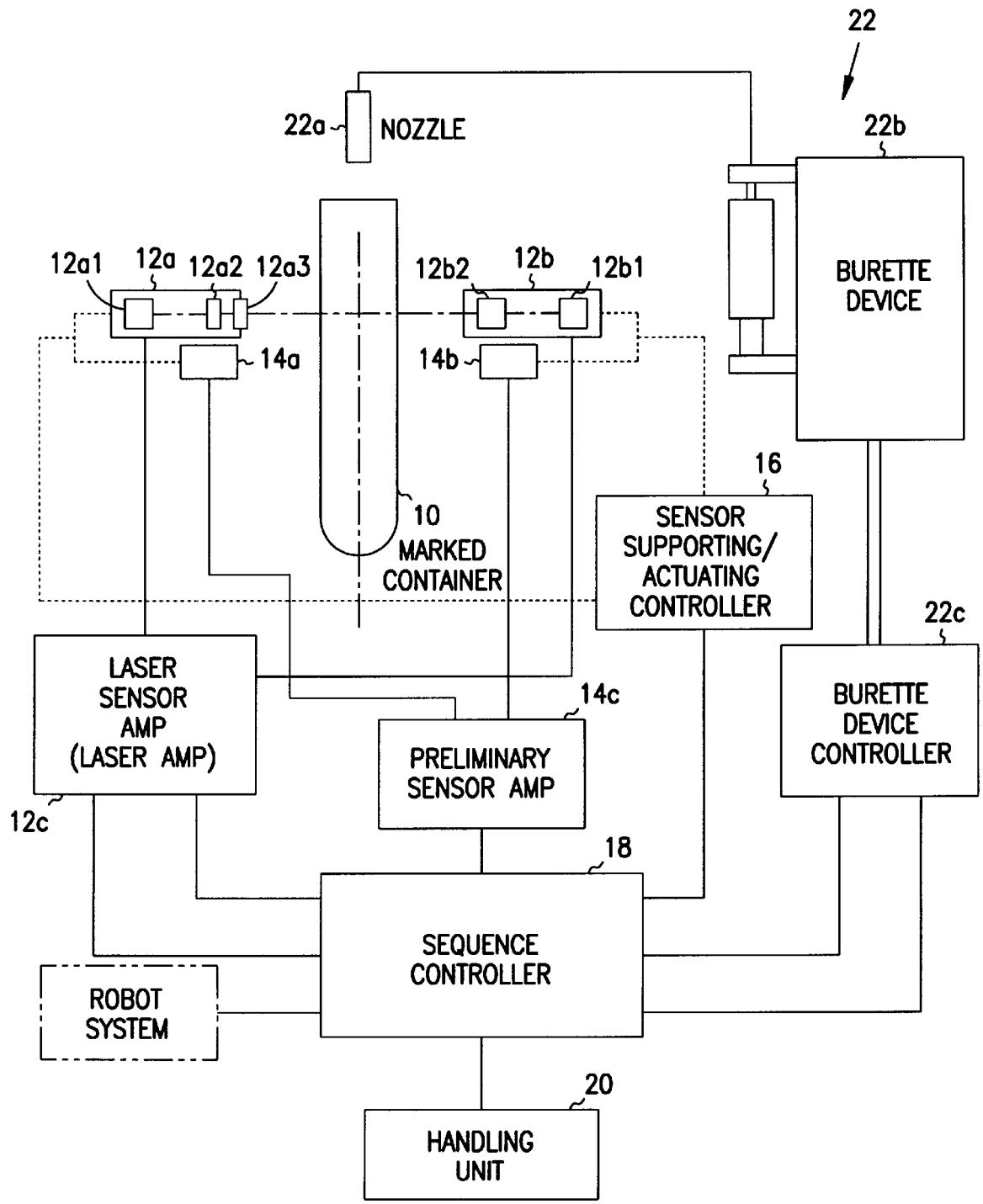
FIG. 6 is a schematic diagram of an automatic filling system according to a preferred embodiment of the present invention which is applicable to a container that has been pretreated by the analytic container pretreating apparatus.
Figure 7A:
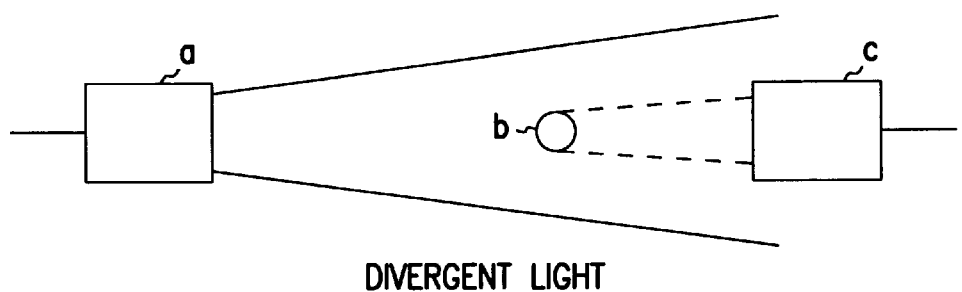
FIG. 7(a) is a diagram illustrative of principles of detecting a liquid level with the automatic filling system when it uses divergent light.
Figure 7B:
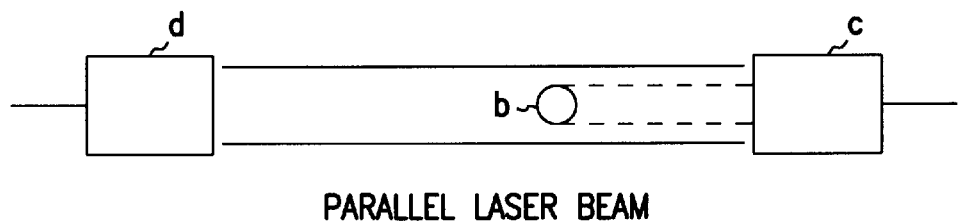
FIG. 7(b) is a diagram illustrative of principles of detecting a liquid level with the automatic filling system when it uses a parallel laser beam.
Figure 8:
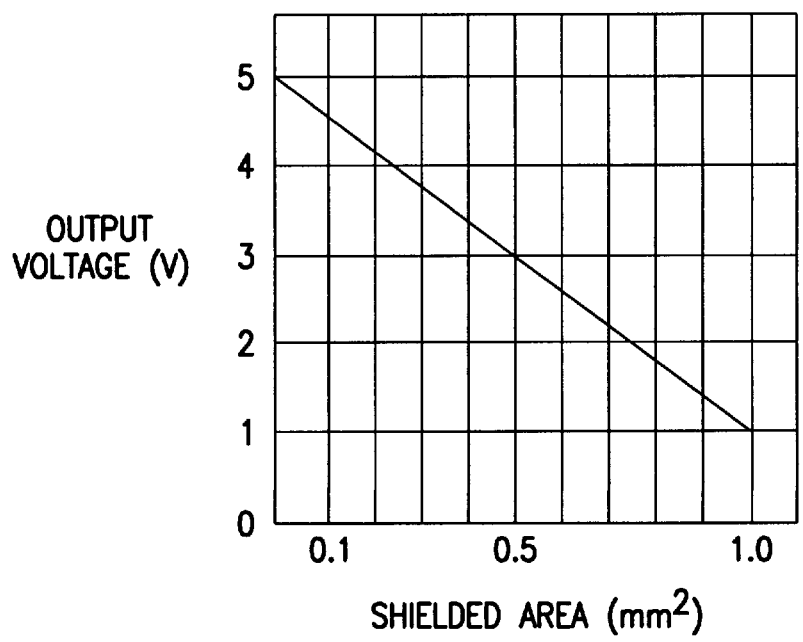
FIG. 8 is a graph showing the relationship between a shielded area and an analog output voltage signal when a parallel laser beam is used for detecting a liquid level in the automatic filling system.
Figure 9:
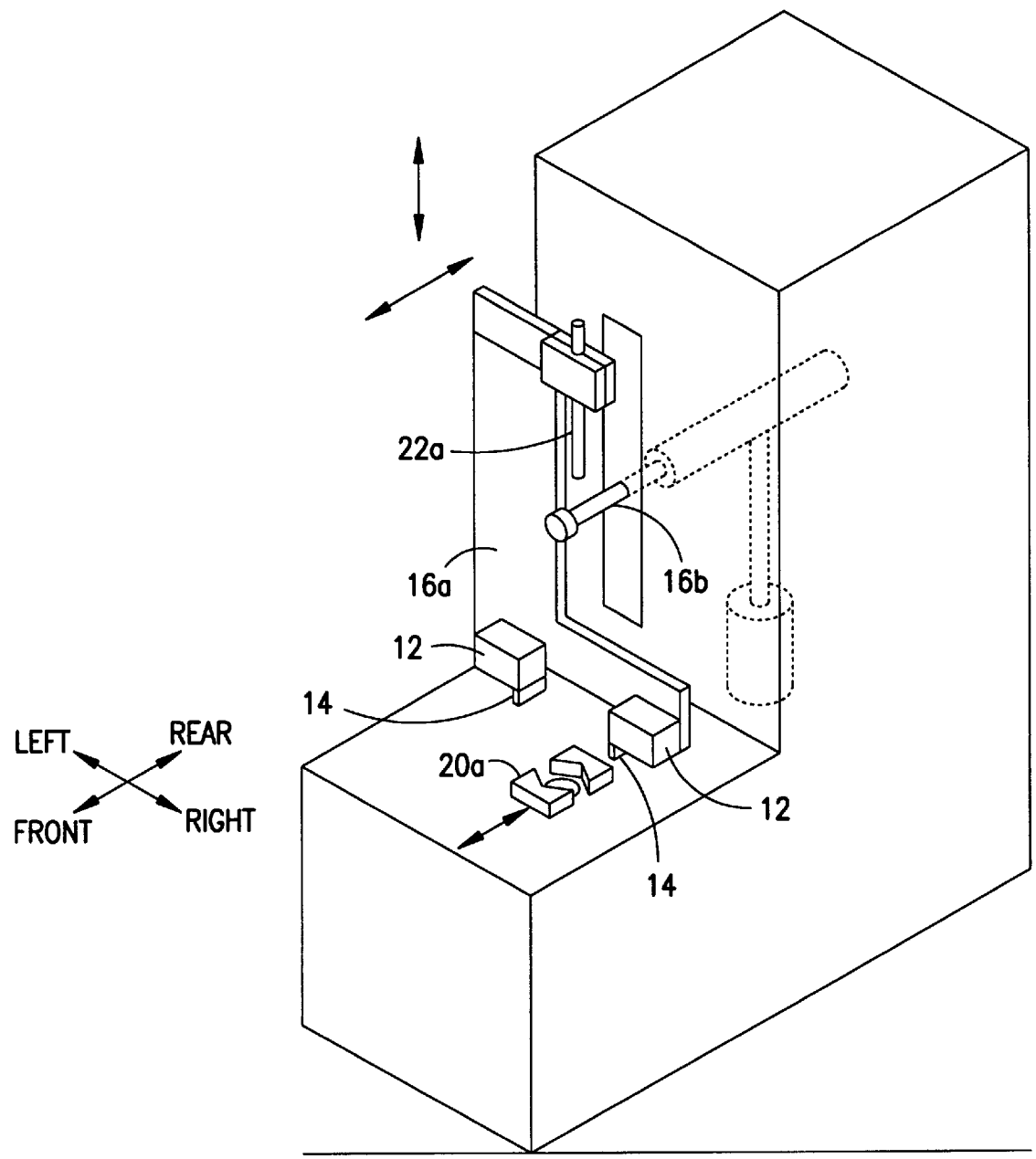
FIG. 9 is a perspective view of the automatic filling system shown in FIG. 6.
Figure 10:
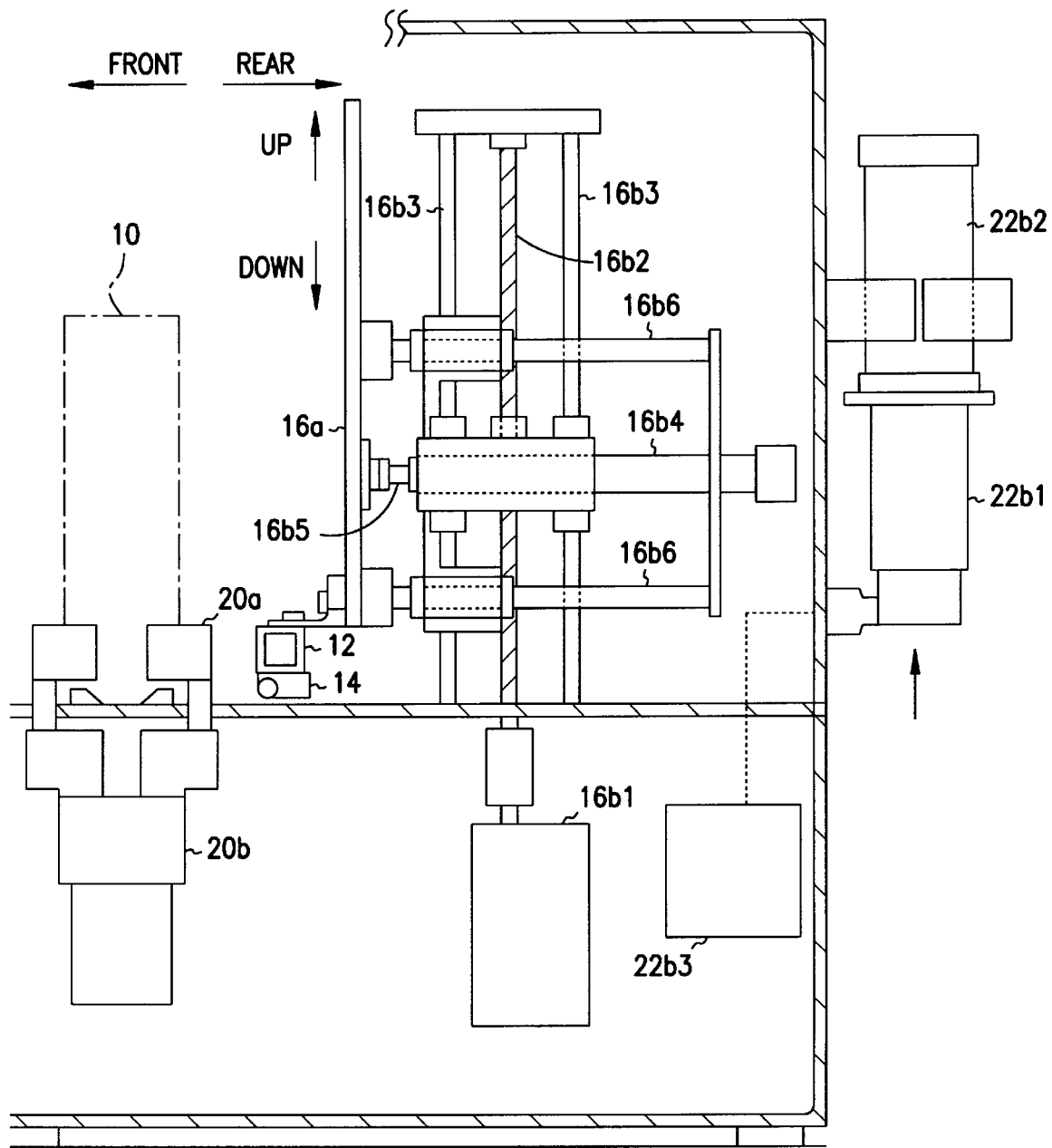
FIG. 10 is a vertical cross-sectional view of the automatic filling system shown in FIG. 9.
Figure 11:
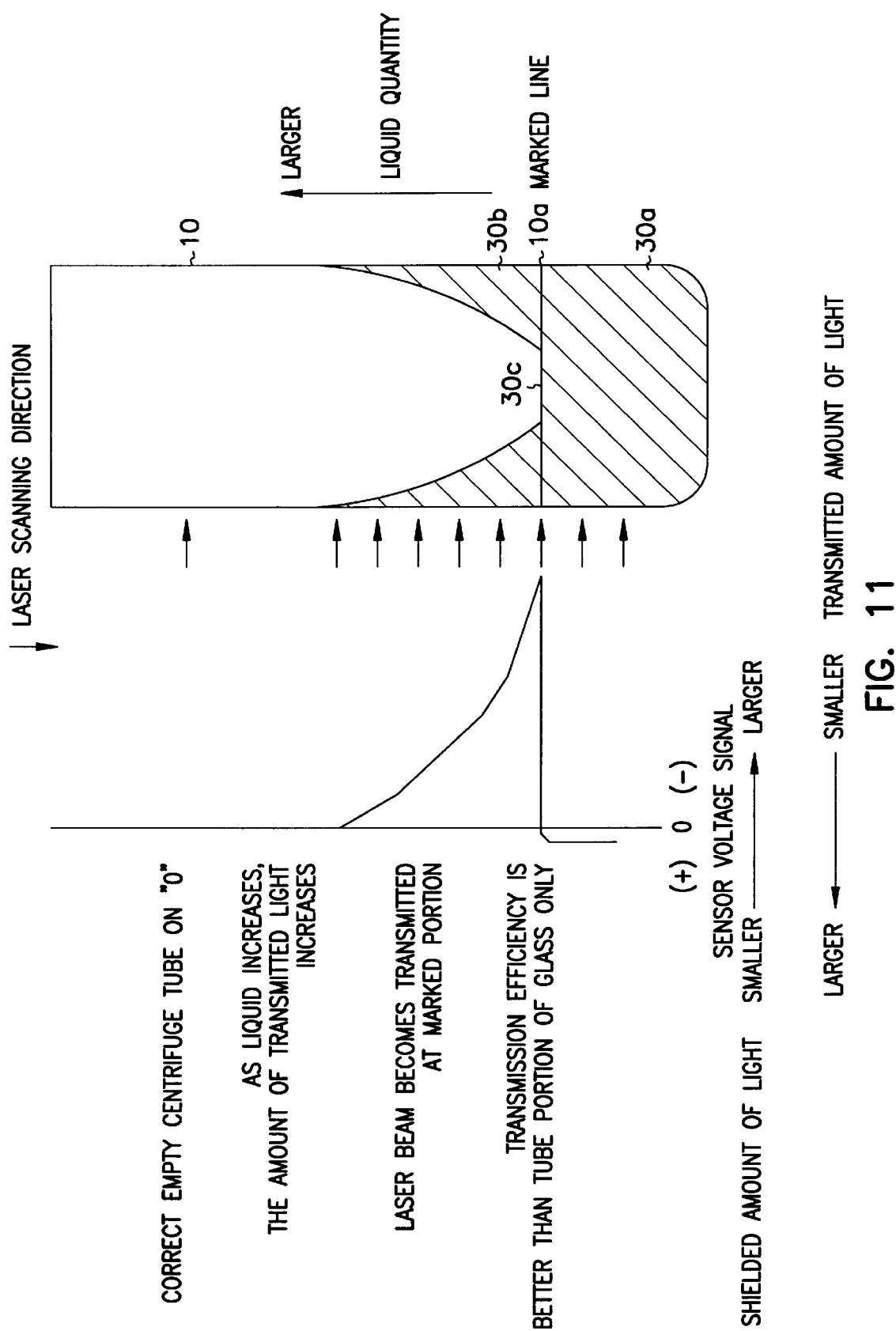
FIG. 11 is a diagram illustrative of an operation of the automatic filling system for detecting a liquid level.
Figure 12:
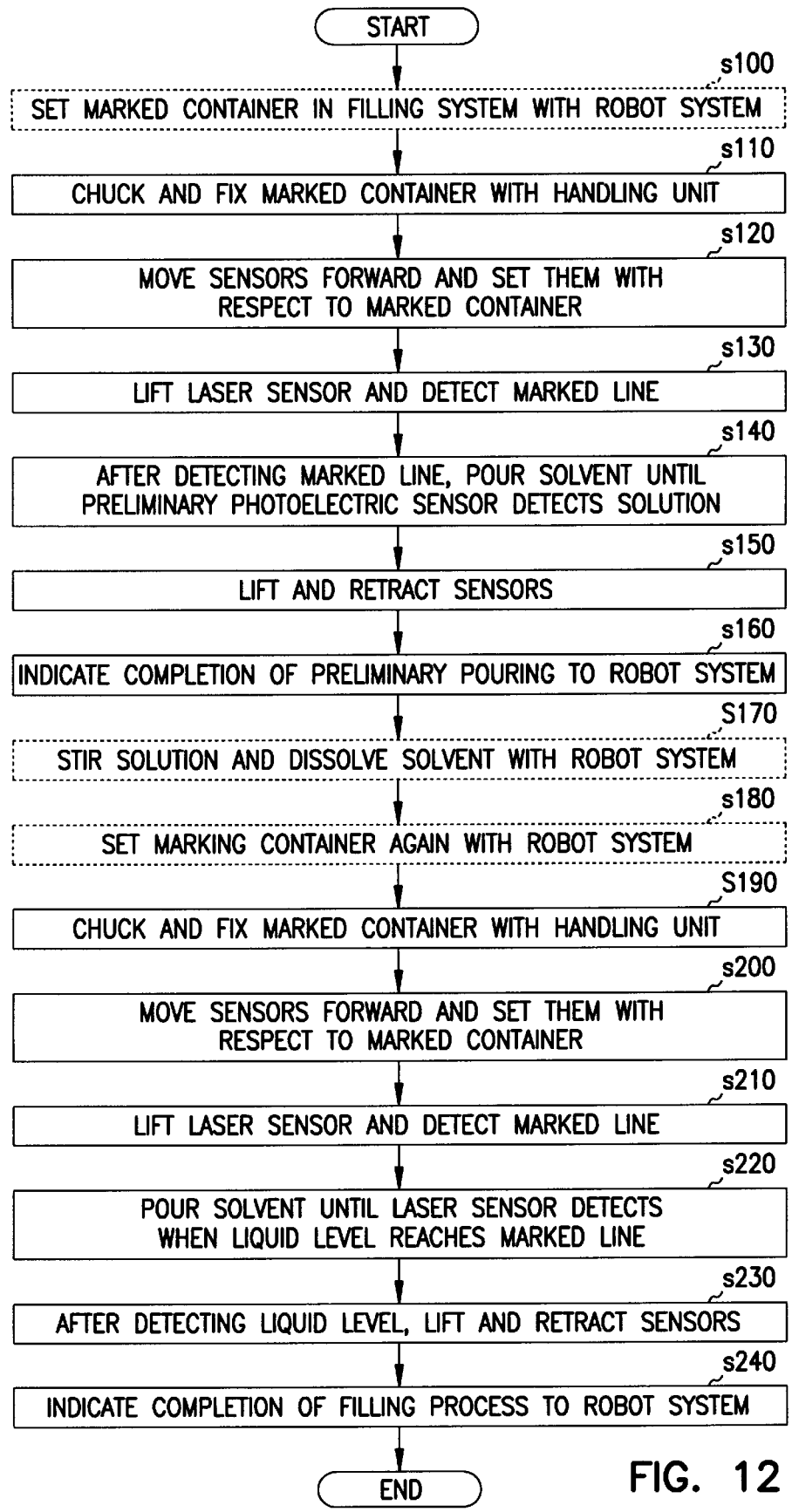
FIG. 12 is a flowchart of a control sequence of the automatic filling system.

FIG. 6 shows an arrangement of the automatic filling system; FIGS. 7 and 8 illustrate principles of detecting a liquid level with a laser sensor; FIG. 9 shows an appearance of the automatic filling system; FIG. 10 is a vertical cross-sectional view of the automatic filling system; FIG. 11 is a diagram illustrative of an operation of the automatic filling system; and FIG. 12 is a flowchart of a control sequence of the automatic filling system.

As shown in FIGS. 6, 9, and 10, the automatic filling system primarily comprises a marked container 10, a laser sensor 12, a preliminary photoelectric sensor 14, a sensor supporting/actuating mechanism 16, a sequence controller 18, a handling unit 20, and a burette device 22. These components will be described below with reference to FIGS. 6 through 10.

The automatic filling system employs a detecting process with a laser beam for the following reasons:

A conventional photoelectric sensor can detect an object out of contact therewith, and is widely used to detect the presence or position of an object. In the photoelectric sensor, as shown in FIG. 7(a), light is emitted from a light-emitting element (light emitter) "a" to an object "b", and the light that has passed through the object "b" is detected by a light-detecting element "c". The position, etc. of the object "b" is detected based on the amount of detected light. The photoelectric sensor uses visible light from a light source, the light is not parallel light (it is divergent light), and the amount of light is attenuated. Consequently, there is a limitation on the size of the object and the distance up to the sensor, and hence small objects and distances over which objects are detected have suffered limitations. Therefore, the conventional photoelectric sensor cannot be used to detect liquid levels.

As a result of various studies, the inventor has found that a light emitter for emitting a parallel laser beam can be used as the light source for the light emitter "d" of the conventional photoelectric sensor (such a sensor is referred to as a laser sensor).

The parallel laser beam has a constant optical axis, and reaches a light-detecting element from the light source without being diverged. If an light shield is present in the optical path, then the image of the light shield within a laser-illuminated region is projected onto the light-detecting element without a size increase or reduction irrespective of where the light shield may be positioned in the laser-illuminated region.

Therefore, since the laser sensor allows the size of the light shield to be detected as a change in the amount of light, slight differences or changes in dimensions such as the height, shape, profile, etc. of the light shield can accurately be determined. The laser sensor is thus suitable for the detection of delicate liquid levels.

The inventor has constructed an automatic filling system for filling a liquid up to a marked line on a container by detecting the liquid level and the marked line accurately with a laser sensor.

(1) As shown in FIGS. 6 and 11, the marked container 10 comprises a measuring flask or test tube for holding a solution, which has an open upper end and a closed spherical lower end and is made of a colorless, transparent material such as glass. The marked container 10 has a marked line 10a on its surface at the position of a liquid level of a solution in a certain quantity (e.g., 50 ml) (see FIG. 11). A solvent that can be poured into the marked container 10 may be either an inorganic solvent or an organic solvent (some solvents are not permissible). The marked container 10 can be set in and removed from the automatic filling system by a robot system (not shown). After a solution is preliminarily poured into the marked container 10, it is stirred.

One example for use as the marked container 10 is a centrifuge tube. However, the marked container 10 is not limited to a centrifuge tube, but may be any of various other containers provided it has a marked line and a transparent portion including at least the marked line (e.g., a container having a portion colored brown). In this embodiment, the marked container 10 has a single marked line. However, the number of marked lines on the marked container according to the present invention is not limited to 1, but the marked container may have two or more marked lines.

(2) The laser sensor 12 detects the liquid level of a solution in the marked container 10 and the marked line 10a with a parallel laser beam, and outputs an analog voltage signal depending on the liquid level and the marked line 10a. The laser sensor 12 mainly comprises a laser emitter 12a, a laser detector 12b, and a laser amplifier 12c. The output voltage signal from the laser sensor 12 is inputted to the sequence controller 18.

The laser emitter 12a serves to emit a parallel laser beam to the marked container 10. The laser emitter 12a comprises a light source 12a1 such as a semiconductor laser for radiating a laser beam, a lens 12a2 for converging the laser beam into a parallel laser beam, and a slit 12a3 for radiating the converged laser beam with a predetermined diameter. In the embodiment, the light source 12a1 emits a laser beam having a wavelength of 670 nm and radiates the laser beam in a pulse radiation mode. The light source 12a1 has a maximum output of 0.8 mW and an average output of 0.3 mW. The slit 12a3 comprises a circular slit having an opening diameter of 1 mm. These numerical values are given by way of example only, and the present invention is not limited to those numerical values.

The laser detector 12b detects a parallel laser beam that has passed through the marked container 10, and outputs an analog voltage signal depending on the amount of light detected thereby. The output voltage signal is inputted to the laser amplifier 12c. The laser detector 12b mainly comprises a lens 12b2 for focusing the laser beam onto a light-detecting element 12b1, and the light-detecting element 12b1 for converting the focused parallel laser beam into an electric signal (analog voltage signal or the like).

The analog output voltage signal of the light-detecting element 12b1 is related to a shielded area of the parallel laser beam as shown in FIG. 8. When the parallel laser beam is applied to the liquid level or the marked line 10a, the parallel laser beam is blocked thereby, changing a shielded area or equivalent shielded area as shown in FIG. 11. Therefore, the liquid level and the marked line 10a can be detected based on the analog output voltage signal of the light-detecting element 12b1. The above details are given by way of example only, and the present invention is not limited thereto.

The laser amplifier 12c supplies a power source to the laser emitter 12a for laser emission, and amplifies and outputs an analog output voltage signal from the laser detector 12b. An output voltage signal from the laser amplifier 12c is inputted to the sequence controller 18 as described above.

(3) The preliminary photoelectric sensor 14 serves to detect a liquid level which is a given distance below the marked line 10a. The preliminary photoelectric sensor 14 comprises a light emitter 14a, a light detector 14b, and a preliminary sensor amplifier 14c (these are known in the art). A detected liquid level signal from the preliminary photoelectric sensor 14 is inputted to the sequence controller 18. Specifically, a solution is poured into the marked container 10 up to a liquid level detected by the preliminary photoelectric sensor 14, and a certain amount of solvent is quickly poured preliminarily before a filling process (such a pouring process is referred to as a preliminary pouring process). The preliminary photoelectric sensor 14 comprises a liquid level sensor for detecting a liquid level with divergent light shown in FIG. 7(a). Therefore, the detecting accuracy of the preliminary photoelectric sensor 14 is somewhat lower than the detecting accuracy of the laser sensor 12. However, since an accurate amount of solvent is poured using the laser sensor 12 after the preliminary pouring process using the preliminary photoelectric sensor 14, the accuracy of the final filling process carried out by the automatic filling system according to the embodiment is high.

If the filling process were carried out using only the laser sensor 12, but not the preliminary photoelectric sensor 14, then since the liquid level increases only slightly, the filling process would need a long period of time. According to the present embodiment, the preliminary pouring process is carried out quickly based on the detected signal from the preliminary photoelectric sensor 14, and thereafter the filling process is performed using the laser sensor 12. Therefore, the time required for the filling process is shortened.

(4) The sensor supporting/actuating mechanism 16 has a support member 16a supporting the laser emitters 12a, 14a and the laser detectors 12b, 14b of the laser sensor 12 and the preliminary photoelectric sensor 14, and an actuating mechanism for actuating the support member 16a back and forth and vertically. The sensor supporting/actuating mechanism 16 serves to scan the laser sensor 12 and the preliminary photoelectric sensor 14 vertically along the marked container 10 (supported and fixed vertically by the handling unit 20).

As shown in FIG. 9, the support member 16a is of a substantially L-shaped structure. The laser emitters 12a, 14a and the laser detectors 12b, 14b are fixed to and supported on respective horizontally opposite ends of a lower portion of the support member 16a with the laser sensor 12 being positioned above the preliminary photoelectric sensor 14. Optical axis adjustments between the laser emitters 12a, 14a and the laser detectors 12b, 14b are made by screws.

As shown in FIGS. 9 and 10, the actuating mechanism comprises a vertical actuator such for example as a reversible motor 16b1 having a positioning accuracy of ±0.1 mm or less, a feed screw 16b2, guide rods 16b3, a horizontal actuator such for example as an air cylinder 16b4 having a stroke of 50 mm, a rod 16b5 thereof, and guide rods 16b6 thereof. Based on drive forces produced by these actuators, the actuating mechanism actuates and positions the sensors 12, 14 through the support member 16a.

As shown in FIGS. 9 and 10, the support member 16a is fixed to the tip end of the cylinder rod 16b5. When the cylinder rod 16b5 moves back and forth, the support member 16a is moved back and forth without wobbling while being guided by the guide rods 16b6. The cylinder 16b4 is vertically movable by the feed screw 16b2. Therefore, when the feed screw 16b2 is rotated about its own axis by the motor 16b1, the cylinder 16b4 is moved vertically without wobbling while being guided by the guide rods 16b3. As a consequence, the support member 16b is vertically movable without wobbling by the cylinder rod 16b5.

(5) The sequence controller 18 is supplied with detected signals from the laser sensor 12 and the preliminary photoelectric sensor 14 and various other signals, and outputs actuating signals to the actuators for enabling the automatic filling system to carry out the filling process according to a predetermined operation procedure. The sequence controller 18 comprises a microcomputer, a memory, an interface, etc. which are known in the art. Details of the operation procedure will be described later on.

The sequence controller 18 is also supplied with input signals from outside of the automatic filling system, including a signal representing whether the marked container 10 is set in or removed from the robot system (the signal is related to a closing movement of a chuck 20*a* of the handling unit 20), a signal for forcibly resetting the automatic filling system, a signal representing the completion of a chucking operation of the robot system (the signal is related to an opening movement of the chuck 20*a* of the handling unit 20), etc. The sequence controller 18 also outputs signals outside of the automatic filling system, including a signal representing the completion of a preliminary pouring process, a signal representing the completion of a filling process, a signal representing the completion of opening and closing movements of the chuck 20*a* (for timed operation in synchronism with the robot system), alarm signals (indicative of a handling error, a marked line 10*a* detection error, and burette device 22*b* upper and lower limit errors). The sequence controller 18 is also supplied with manual signals including signals from manual switches in a control box (not shown), i.e., signals representing opening and closing movements for the chuck 20*a*, back-and-forth movement for the sensors 12, 14, vertical fine-adjustment movement for the sensors 12, 14, drawing/discharging operations, resetting, and an emergency stop. These input and output signals are non-contact signals whose levels range from DC 0 V to 30 V.

(6) The handling unit 20 serves to support and fix the marked container 10 during the filling process, and keep the positional relation between the laser sensor 12 and the preliminary photoelectric sensor 14 unchanged. As shown in FIGS. 9 and 10, the handling unit 20 comprises a chuck 20*a* for gripping the marked container 10 in the back-and-forth direction, and an actuator 20*b* such for example as an air cylinder for moving the chuck 20*a* symmetrically about the marked cylinder 10.

(7) The burette device 22 serves to draw and discharge a solvent. The burette device 22 comprises a nozzle 22*a* whose tip end can face downwardly toward the marked container 10 or can be inserted downwardly into the marked container 10 for introducing a solvent delivered from a burette unit 22*b* into the marked container 10, the burette unit 22*b* having a piston (plunger) 22*b*1 and a cylinder 22*b*2 and an actuator 22*b*3 for actuating the piston, for thereby pressurizing the solvent stored therein to deliver the solvent to the nozzle 22*a*, and a burette controller 22*c* for operating the actuator of the burette unit 22*b* according to an output signal from the sequence controller 18. As shown in FIG. 9, the nozzle 22*a* is mounted on an upper portion of the support member 16*a* which supports the laser sensor 12 and the preliminary photoelectric sensor 14, for movement with these sensors 12, 14. The actuator 22*b*3 comprises a stepping motor, for example, and can deliver the solvent with an accuracy of ±0.01%, for example. A solvent delivery pipe (omitted from illustration in FIG. 9) from the burette unit 22*b* to the nozzle 22*a* is made of polytetrafluoroethylene ("Teflon" manufactured by Du Pont, U.S.A.)

The burette device 22 is associated with a three-way solenoid-operated valve for switching between pipes to deliver a solvent from the burette unit 22*b* to the nozzle 22*a* or to draw a solvent into the burette unit 22*b*.

Principles of detection in the filling process carried out by the automatic filling system according to the embodiment will be described below with reference to FIG. 11.

In the embodiment, the laser sensor 12 applies a laser beam to the marked line 10*a* in the filling process. In FIG. 11, the marked line 10*a* is not taken into account, and the manner in which a solution 30*a* in the marked container 10 increases is replaced with the manner in which the position where the laser beam is applied shifts downwardly, scanning the marked container 10 with the laser sensor 12. The marked line 10*a* is shown only when the solution is filled up to the marked line 10*a*.

An empty portion of the marked container 10 which is above a solution and is free of a solution 30*a* is detected by the laser sensor 12. Assuming that a detected output signal from the laser sensor 12 at this time is "0", the laser sensor 12 is corrected for "0".

As a solvent is gradually poured and the liquid level rises in the marked container 10, a meniscus 30*b* elevated due to the surface tension of the solution 30*a* is detected. As shown in FIG. 11, the meniscus 30*b* progressively increases the amount of shielded light toward a liquid level 30*c*, and hence the output voltage from the laser sensor 12 decreases in the direction toward the liquid level 30*c*. At the position of the liquid level 30*c*, the output voltage from the laser sensor 12 is minimum because the amount of shielded light is maximum. Below the liquid level 30*c*, the marked container 10 is filled with the solution, and the amount of shielded light is smaller than in the empty portion of the marked container 10. Consequently, the amount of light transmitted through the filled portion of the marked container 10 below the liquid level 30*c* is larger. The output voltage from the laser sensor 12 thus changes from the minimum output voltage (negative maximum output voltage) to the maximum output voltage (positive maximum output voltage) across the liquid level. The position where the minimum output voltage is detected corresponds to the liquid level 30*c*. The minimum output voltage can be detected when the output voltage from the laser sensor 12 is compared with a predetermined value by a comparator in the sequence controller 18. The position where this voltage signal is detected is the position of the liquid level 30*c*. As a result, the liquid level can be detected highly accurately. Since the marked line blocks light, it can also be detected as accurately as the liquid level. The amount of shielded light is maximum when the liquid level coincides with the marked line 10*a*, and such a condition can accurately be detected by the laser sensor 12.

In the embodiment, the laser sensor 12 is lowered downwardly and thereafter lifted upwardly while scanning the marked container 10, thereby to detect the marked line 10*a*. When the marked line 10*a* is detected, the laser sensor 12 is stopped. Then, the solvent is gradually poured into the marked container 10, and the liquid level as it gradually rises is detected by the laser sensor 12. A detected result is the same as when the laser sensor 12 scans the marked container 10 downwardly as shown in FIG. 11. Since the marked line is also detected, it is necessary to establish a predetermined value for comparison in view of the detection of the marked line.

Overall operation of the automatic filling system according to the embodiment will be described below with reference to FIG. 12. In FIG. 12, steps are represented by s100~s240, and the operation of the automatic filling system is shown by solid lines whereas the operation of the robot system by broken lines.

The automatic filling system and the robot system are reset into initial conditions in advance.

When the automatic filling system is started, the robot system sets the marked container 10 in the automatic filling system (s100). At this time, the robot system outputs a robot set signal which is inputted to the sequence controller 18. Then, the handling unit 20 chucks the marked container 10 in response to the robot set signal (s110).

The laser sensor 12 and the preliminary photoelectric sensor 14 are moved forward and set in position. Specifically, upon forward movement of the support member 16a, these sensors 12, 14 are simultaneously moved forward while they are at an upper limit end. After the sensors 12, 14 are positioned in sandwiching relation to the axis of the marked container 10, the sensors 12, 14 are lowered to a lower limit end and set in position (s120).

Then, the sensors 12, 14 are lifted along the axis of the marked container 1, and the laser sensor 12 detects the marked line 10a (s130). When the laser sensor 12 detects the marked line 10a, the sensors 12, 14 are stopped and fixed in position.

Then, the burette device 22 pours a solvent into the marked container 10 until the preliminary photoelectric sensor 14 detects the solution (s140), whereupon the preliminary pouring process is finished.

Then, the sensors 12, 14 are lifted and retracted (s150).

Then, the end of the preliminary pouring process is indicated to the robot system (s160).

Then, the robot system grips the marked container 10, is retracted, and stirs the solution to dissolve the solvent (s170). After the solution is stirred to dissolve the solvent, the robot system sets the marked container 10 again in the automatic filling system (s180).

Then, the handling unit 20 chucks the set marked container 10, thereby fixing it in position (s190).

Then, as with the step s120, the laser sensor 12 and the preliminary photoelectric sensor 14 are set in position with respect to the marked container 10 (s200).

Then, the laser sensor 12 and the preliminary photoelectric sensor 14 are elevated along the axis of the marked container 10 to detect the marked line 10, as with the step s130 (s210).

Then, in response to a detected signal from the laser sensor 20, the solvent is poured into the marked container 10 until the liquid level reaches the marked line 10a (s220).

Then, after the laser sensor 12 detects when the liquid level reaches the marked line 10a (the solution fills the marked container 10 up to the marked line 10a), the sensors 12, 14 are lifted and retracted (s230).

Then, the end of the filling process is indicated to the robot system (s240).

While preferred specific embodiments have been described above, the present invention is not limited to the illustrated embodiments, but may be embodied in other forms within the technical scope thereof.

In the above embodiments, the pretreating apparatus has been described as carrying out a process of pretreating the marked container for the automatic filling system. However, the analytic container that can be pretreated according to the present invention is not limited to the container of the type described above. Instead, the pretreating apparatus may be used to clean and dry other analytic containers. The analytic container that can be pretreated according to the present invention is not limited to a transparent container like the above marked container, but may be a nontransparent container for precision analysis to achieve increased analytic accuracy using the container.

In the pretreating apparatus according to the embodiment, the feed robot is automatically operated by the unit controller 6. However, the present invention is not limited to such automatic operation of the feed robot, but covers manual operation of the feed robot.

According to the present invention, as described above, the container for holding an analytic liquid is automatically and continuously processed for various pretreating operations prior to an analysis, including debubblizing and cleaning processes, and preferably a drying process for drying away (removing) the cleaning liquid. Therefore, the container is made free of obstacles to the transmission of detected light through the container, allowing a process of filling a liquid in the container to be carried out with good optical accuracy.

INDUSTRIAL APPLICABILITY

The automatic filling system according to the present invention permits a solution, which is to be analyzed, to be prepared with precision, such as in a filling process for filling a material to be analyzed and a solvent in a container, for thereby realizing an automatic system in the art of an automatic measuring analysis of various materials.

We claim:

1. An automatic filling system for automatically carrying out a filling process to fill a solution, which comprises a material to be analyzed that is dissolved in a solvent, up to a desired position on a marked line on a container, comprising:

a container having a marked line and including a transparent portion where said marked line is present;

liquid pouring means for pouring a given liquid into said container;

laser beam emitting means for emitting a parallel laser beam at said marked line at said portion of the container;

laser beam detecting means for detecting the laser beam emitted from said laser beam emitting means and having passed through said container at said marked line, said laser beam detecting means to detect an amount of the laser beam having passed through said container at said portion;

pouring control means for controlling said liquid pouring means based on the amount of the laser beam which has been detected by said laser beam detecting means, said pouring control means to fill said liquid up to a desired liquid level based on said marked line and to control said liquid pouring means to stop pouring based on a laser beam amount detected by said laser beam detecting means at said portion corresponding to said marked line;

auxiliary liquid level detecting means for detecting an auxiliary liquid level at least below said marked line on said container; and preliminary pouring means for filling said liquid up to said auxiliary liquid level in said container through detection by said auxiliary liquid level detecting means prior to said filling process.

2. The automatic filling system according to claim 1, further comprising:

actuating means for simultaneously moving said laser beam emitting means and said laser beam detecting means at least along an axis of said container;

marked line detecting means for detecting said marked line based on a change in an amount of the laser beam which has been detected by said laser beam detecting means while said laser beam emitting means and said laser beam detecting means are being moved by said actuating means; and means for setting said laser beam emitting means and said laser beam detecting means to the desired position with respect to said marked line based on the marked line detected by said marked line detecting means.

3. The automatic filling system according to claim 1, wherein said auxiliary liquid level detecting means comprises a photoelectric sensor disposed below said marked line.

4. The automatic filling system according to claim 3, wherein said photoelectric sensor comprises a light emitter and a light detector.

5. The automatic filling system according to claim 3, wherein said preliminary pouring means comprises a burette device.

6. A method for filling a container comprising:

coupling a photoelectric sensor below a laser sensor on a support member;

applying a laser beam from the laser sensor to a marked container;

moving the support member in a vertical direction along the container;

scanning the container having a marked line until the laser sensor senses the marked line;

stopping movement of the laser sensor at the marked line;

pouring liquid into the container until the photoelectric sensor senses a level of the liquid; and pouring additional liquid into the container until the laser sensor senses a meniscus of the liquid.

7. The method as recited in claim 6, further comprising stirring the liquid prior to pouring additional liquid into the container.

* * * * *